(12) United States Patent
Pernodet et al.

(10) Patent No.: US 9,833,393 B2
(45) Date of Patent: Dec. 5, 2017

(54) METHOD AND COMPOSITIONS FOR TREATING SKIN

(71) Applicant: ELC Management LLC, Melville, NY (US)

(72) Inventors: Nadine Pernodet, Huntington Station, NY (US); Edward Pelle, Valley Stream, NY (US)

(73) Assignee: ELC Management LLC, Melville, NY (US)

( * ) Notice: Subject to any disclaimer, the term of this patent is extended or adjusted under 35 U.S.C. 154(b) by 17 days.

(21) Appl. No.: 14/864,207

(22) Filed: Sep. 24, 2015

(65) Prior Publication Data

US 2017/0087071 A1    Mar. 30, 2017

(51) Int. Cl.
*A61Q 17/04* (2006.01)
*A61Q 19/08* (2006.01)
*A61K 8/36* (2006.01)
*A61K 8/92* (2006.01)

(52) U.S. Cl.
CPC .............. *A61K 8/361* (2013.01); *A61K 8/922* (2013.01); *A61Q 17/04* (2013.01); *A61Q 19/08* (2013.01)

(58) Field of Classification Search
CPC ................ A61K 31/519; A61K 31/437; A61K 31/5377; A61K 31/538; A61K 8/361; A61K 8/922; C07D 487/04; C07D 487/14; C07D 519/00; A61Q 17/04; A61Q 19/08
See application file for complete search history.

(56) References Cited

U.S. PATENT DOCUMENTS

| | | | |
|---|---|---|---|
| 3,439,088 A | 4/1969 | Edman | |
| 3,818,105 A | 6/1974 | Coopersmith et al. | |
| 5,077,211 A | 12/1991 | Yarosh | |
| 5,190,762 A | 3/1993 | Yarosh | |
| 5,272,079 A | 12/1993 | Yarosh | |
| 5,296,231 A | 3/1994 | Yarosh | |
| 6,361,806 B1 * | 3/2002 | Allen | A61K 31/015 424/401 |
| 8,193,155 B2 | 6/2012 | Maes | |
| 2005/0106194 A1 | 5/2005 | Schiltz | |
| 2006/0216254 A1 * | 9/2006 | Majmudar | A61K 8/97 424/62 |

FOREIGN PATENT DOCUMENTS

| | | |
|---|---|---|
| DE | 102008044700 | 2/2010 |
| EP | 1214048 B1 | 6/2002 |
| EP | 1801226 | 6/2007 |
| WO | WO-01/17498 | 3/2001 |
| WO | WO-2013055315 A1 | 4/2013 |

OTHER PUBLICATIONS http://www.gnpd.com; Mintel; Caldrea Essential Collection Ginger Honey Body Oil; Record ID 2561343; Caldrea; Skincare; Body Care; USA; Jul. 2014.
http://www.gnpd.com; Mintel; Kadria Skincare Balancing Face Oil; Face/Neck Care; Record ID 2320474; UK; May 2014.
PCT International Search Report: International Application No. PCT/US2016/050868; dated Dec. 23, 2016; Completion Date: Dec. 23, 2016.
PCT Written Opinion of the International Searching Authority; International Application No. PCT/US2016/050868; Completion Date: Dec. 23, 2016; dated Dec. 23, 2016.

* cited by examiner

*Primary Examiner* — Audrea Buckley
(74) *Attorney, Agent, or Firm* — Julie Blackburn

(57) ABSTRACT

A method for increasing and/or synchronizing per1 gene expression in skin cells having decreased, irregular, or asynchronous per1 gene expression comprising treating the skin cells with an effective amount of a polyunsaturated omega-6 fatty acid.

11 Claims, No Drawings

METHOD AND COMPOSITIONS FOR TREATING SKIN

TECHNICAL FIELD

The invention is in the field of methods for treating skin cells to increase per1 gene expression in order to ameliorate the adverse effects of natural aging of skin, UV radiation, environmental toxins, environmental pollution, and the like, and the compositions used in the method.

BACKGROUND OF THE INVENTION

It is well known that environmental aggressors such as UV radiation, environmental pollution, environmental toxins, physiological stress, and the natural process of aging can be very detrimental to skin. The skin on the face is made up of keratinocytes, fibroblasts, melanocytes, T-cells and so on. Environmental aggressors cause damage to DNA of skin cells and affects the cellular circadian rhythm in general. The body's natural circadian rhythms are synchronized such that during exposure to environmental aggressors—usually during daylight hours—certain genes in the cells are activated to produce proteins that protect the cells against damage.

Genes associated with natural bodily circadian rhythms have been identified and include the clock (Circadian Locomotor Output Cycles Kaput) gene and the per1 (Period Homolog 1) gene, both of which encode proteins (CLK and PER1) that regulate circadian rhythms. Clock and per1 genes are also present in skin cells. The induction of per1 gene expression initiates a program of cellular activity that is associated with biological processes that take place at night (e.g. repair). It is known that skin cells exposed to environmental aggressors will often exhibit decreased, irregular, or asynchronous clock or per1 gene expression. This in turn causes disruption of normal circadian rhythm in the exposed skin cells. Over a prolonged period of time disruption of normal cellular circadian rhythm and synchronicity can accelerate the natural aging process of skin which leads to wrinkles, fine lines, skin laxity, uneven pigmentation, age spots, mottling, and the like.

For this reason it is very advantageous to maintain natural cellular circadian rhythm to the greatest extent possible. To date, the only known mechanisms for synchronizing skin cells are to (1) starve the cells for an extended period of time by removing nutrients and energy sources, and then suddenly resupply the nutrients; or (2) treating the skin cells with a peptide having the C.T.F.A. name Tripeptide-32. The practical difficulties in starving skin cells not in culture are obvious. In addition, the ingredient known to have this activity is expensive.

It has been discovered that ingredients containing at least one linoleic acid moiety are an effective stimulator of per1 gene expression in skin cells. The ability to increase per1 gene expression in skin cells means that skin cells with irregular or decreased synchronicity will become synchronized (e.g. all cells exhibit same level of per1 gene expression at the same time). When skin cells are synchronized, treatment of the skin cells with active ingredients that repair cellular damage are the most effective. It is most beneficial to treat skin cells to increase per1 gene expression and thereby cause the treated cells to be synchronized so that the active ingredients in skin treatment products may be optimally beneficial to the skin cells. In one most preferred embodiment of the invention the skin cells are treated with an ingredient containing at least one polyunsaturated omega-6 fatty acid to increase per1 gene expression and synchronicity at night prior to retiring.

SUMMARY OF THE INVENTION

The invention is directed to a method for increasing and/or synchronizing per1 gene expression in skin cells having decreased, irregular, or asynchronous per1 gene expression comprising treating the skin cells with an effective amount of a polyunsaturated omega-6 fatty acid.

The invention is also directed to a method for increasing and/or synchronizing per1 gene expression in skin cells having decreased, irregular, or asynchronous per1 gene expression due to the natural aging process comprising treating the skin cells with a polyunsaturated omega-6 fatty acid in an amount sufficient to increase the per1 gene expression of the treated cells.

The invention is also directed to a method for treating skin cells with a regimen comprising:
(a) During the day treating the skin cells with a composition containing chemical or physical UV sunscreens;
(b) At night, treating skin cells that may have decreased, irregular, or asynchronous per1 gene expression due to UV exposure during day hours, with a polyunsaturated omega-6 fatty acid in an amount sufficient to increase and/or synchronize the per1 gene expression of the treated cells.

The invention is also directed to a composition comprising a per1 gene activator consisting of a polyunsaturated omega-6 fatty acid.

DETAILED DESCRIPTION

I. Definitions

All percentages mentioned herein are percentages by weight unless otherwise indicated.

The term "DNA repair enzyme" means an enzyme that is operable to repair DNA base mutagenic damage. Such enzymes are often categorized by the type of DNA damage they repair, for example base excision repair (BER) enzymes, nucleotide excision repair (NER) enzymes; mismatch repair (MMR) enzymes; DNA helicases; DNA polymerases, and so on. For example, DNA lesions such as 8-oxo-7,8-dihydro-2'-deoxyguanosine may be repaired by OGG1 (8-oxoGuanine glycosylase); T-T dimers which may be repaired by NER (nucleotide excision repair) or CPD Photolyase); 6-4 photoproducts (which may be repaired by NER or 6-4 Photolyase); and 06-methyl guanine (which may be repaired by 06-alkyl guanine DNA transferase (AGT)).

"Environmental pollution" means contaminants typically found in the environment such as smog, cigarette smoke, dust, pollen, motor vehicle exhaust, and the like.

"Environmental toxins" means ingredients found in products that consumers may use in day to day life such as cleaning products containing solvents, chemicals found in contaminated ground water, plastic by products, and the like.

The term "polyunsaturated omega-6 fatty acid" means linoleic acid, gamma linolenic acid, calendic acid, eicosadienoic acid, di-homo gamma linolenic acid, arachidonic acid, docosadienoic acid, adrenic acid, docosapentaenoic acid, tetracosatetraenoic acid, tetracosapentaenoic acid or mixtures thereof. The polyunsaturated omega-6 fatty acid may be found in the pure form or in the form of natural plant oils containing the fatty acid.

"Natural aging process" means the natural process of skin aging which includes formation of wrinkles, fine lines, skin laxity, uneven pigmentation, skin mottling, yellowness, and so on.

"per1 gene expression" means the expression of per1 genes in skin cells which may be measured by, among other things, synthesis of proteins transcribed by that gene.

"Physiological stress" means stress conditions to which skin cells may be exposed such as wind burn, itching, chafing, extreme heat or cold.

"skin cells" when used herein means cells that make up skin including but not limited to keratinocyes, melanocytes, fibroblasts, T-cells, and so on.

The term "synchronizing per1 gene expression" means that the per1 gene expression of the treated skin cells is synchronized.

"UV radiation" means ultraviolet radiation in the UVA and UVB wavelength ranges.

II. The Method of the Invention

In the method of the invention at least one polyunsaturated omega-6 fatty acid either alone or in a composition is applied to skin cells, preferably those found on the face or body skin in an amount sufficient to increase and/or synchronize the per1 gene expression in the treated cells. Most preferably the an ingredient containing at least one polyunsaturated omega-6 fatty acid is incorporated into a cosmetic composition and that composition is used to treat skin cells, preferably keratinocytes. In such a case, suggested ranges of the polyunsaturated omega-6 fatty acid are from about 0.000001 to about 40%, preferably from about 0.000005 to 35%, more preferably from about 0.00001 to 25%.

The polyunsaturated omega-6 fatty acid may be in the pure form—either synthetic or extracted from plant sources. Alternatively the polyunsaturated omega-6 fatty acid may be found as a component of plant or vegetable oils. Preferred is where the polyunsaturated omega-6 fatty acid is linoleic acid or gamma linolenic acid. More preferred is where the polyunsaturated omega-6 fatty acid is an essential fatty acid (e.g. not synthesized by the body). Examples of naturally derived oils that contain linoleic acid include but are not limited to borage oil (38.47%), evening primrose oil (74%), canola oil (20%), corn oil (59%), sunflower oil (71%), cottonseed oil (56%), linseed oil (15%), soybean oil (56%), olive oil (7%), extra olive virgin oil (9%), olive pomace oil (10%), peanut oil (31%), rice bran oil (36%), palm oil (10%), palm kernel oil (3%), safflower oil (78%), grape seed oil (73%), poppyseed oil (70%), hemp oil (60%), wheat germ oil (55%), cottonseed oil (54%), walnut oil (51%), sesame oil (45%), rice bran oil (39%), pistachio oil (33%), egg yolk (16%), linseed oil (15%), cocoa butter (5%), macadamia oil (2%) coconut oil (2%), salicornia oil (75%), barberry fig seed oil (65%), walnut oil (51%), sesame oil (45%), argan oil (37%), or olive oil (10%).

In one preferred embodiment the composition topically applied to skin to promote per1 is from *Salvia hispanica* (Chia) seed extract containing from about 12-23% linoleic acid, which may be purchased from Premier Specialties in the form of a mixture of 99.8% of *Salvia hispanica* (Chia) seed extract oil and 0.2% tocopherol.

In another preferred embodiment, the composition topically applied to skin to promote per1 is *Prunus armeniaca* (Apricot) kernel oil containing from about 20-35% linoleic acid.

Preferred plant oils are those containing from about 2 to 100%, preferably from about 10-85%, more preferably from about 15 to 50% of a polyunsaturated omega-6 fatty acid which, in the most preferred embodiment is linoleic acid.

In the method of the invention the polyunsaturated omega-6 fatty acid may be applied to the skin in the form of a skin cream, lotion, foundation makeup, lipstick, concealer, blush, serum, eye shadow, cleanser or toner. The composition may be applied to the skin one or more times per day and in any regimen. The polyunsaturated omega-6 fatty acid may be found in skin cream or lotion or in one or more of a cleanser, toner, or skin treatment product. Preferably the polyunsaturated omega-6 fatty acid is applied to the skin at night, prior to retiring, to maximize the skin's natural repair process.

The composition into which the polyunsaturated omega-6 fatty acid is formulated may contain other ingredients including but not limited to those set forth herein.

IV. Other Ingredients

The composition used in the method of the invention may be in the form of an emulsion, aqueous solution or dispersion, gel, or anhydrous composition. If in the form of an emulsion, it may be a water-in-oil or oil-in-water emulsion. If in the form of an emulsion, the composition may contain from about 1-99%, preferably from about 5-90%, more preferably from about 10-85% water and from about 1-99%, preferably from about 5-90%, more preferably from about 5-75% of oil. If in the form of an aqueous suspension or dispersion, the composition may generally contain from about 1-99.9%, preferably from about 5-95%, more preferably from about 10-90% water, with the remaining ingredients being the active ingredients or other formula ingredients.

A. Humectants

The composition used in the method of the invention may contain one or more humectants. If present, they may range from about 0.1 to 75%, preferably from about 0.5 to 70%, more preferably from about 0.5 to 40%. Examples of suitable humectants include glycols, sugars, and the like. Suitable glycols are in monomeric or polymeric form and include polyethylene and polypropylene glycols such as PEG 4-10, which are polyethylene glycols having from 4 to 10 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectants used in the composition of the invention are $C_{1-6}$, preferably $C_{2-4}$ alkylene glycols, most particularly butylene glycol.

B. Surfactants

It may be desirable for the composition used in the method of the invention to contain one more surfactants, especially if in the emulsion form. However, such surfactants may be used if the compositions are solutions, suspensions, or anhydrous also, and will assist in dispersing ingredients that have polarity, for example pigments. Such surfactants may be silicone or organic based. The surfactants will also aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

1. Organic Nonionic Surfactants

The composition used in the method of the invention may comprise one or more nonionic organic surfactants. Suitable nonionic surfactants include alkoxylated alcohols or ethers, formed by the reaction of an alcohol with an alkylene oxide, usually ethylene or propylene oxide. Suitable alcohols include mono-, di-, or polyhydric short chain (C1-6) alcohols; aromatic or aliphatic saturated or unsaturated fatty (C12-40) alcohols, of cholesterol; and so on.

Cholesterol is suitable, or an aromatic or aliphatic saturated or unsaturated fatty alcohol which may have from 6 to 40, preferably from about 10 to 30, more preferably from about 12 to 22 carbon atoms. Examples include oleyl alcohol, cetearyl alcohol, cetyl alcohol, stearyl alcohol, isostearyl alcohol, behenyl alcohol, and the like. Examples of such ingredients include Oleth 2-100; Steareth 2-100; Beheneth 5-30; Ceteareth 2-100; Ceteth 2-100; Choleth 2-100 wherein the number range means the number of repeating ethylene oxide units, e.g. Ceteth 2-100 means Ceteth where the number of repeating ethylene oxide units ranges from 2 to 100. Derivatives of alkoxylated alcohols are also suitable, such as phosphoric acid esters thereof.

Some preferred organic nonionic surfactants include Oleth-3, Oleth-5, Oleth-3 phosphate, Choleth-24; Ceteth-24; and so on.

Also suitable are alkoxylated alcohols formed with mono-, di-, or polyhydric short chain alcohols, for example those having from about 1 to 6 carbon atoms. Examples include glucose, glycerin, or alkylated derivatives thereof. Examples include glycereth 2-100; gluceth 2-100; methyl gluceth 2-100 and so on. More preferred are methyl gluceth-20; glycereth-26 and the like.

Other types of alkoxylated alcohols are suitable surfactants, including ethylene oxide polymers having varying numbers of repeating EO groups, generally referred to as PEG 12 to 200. More preferred are PEG-75, which is may be purchased from Dow Chemical under the trade name Carbowax PEG-3350.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with C6-30, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

2. Silicone or Silane Surfactants

Also suitable are various types of silicone or silane-based surfactants. Examples include organosiloxanes substituted with ethylene oxide or propylene oxide groups such as PEG dimethicones which are dimethicones substituted with polyethylene glycols including those having the NCI names PEG-1 dimethicone; PEG-4 dimethicone; PEG-8 dimethicone; PEG-12 dimethicone; PEG-20 dimethicone; and so on.

Also suitable are silanes substituted with ethoxy groups or propoxy groups or both, such as various types of PEG methyl ether silanes such as bis-PEG-18 methyl ether dimethyl silane; and so on.

Further examples of silicone based surfactants include those having the generic names dimethicone copolyol; cetyl dimethicone copolyol; and so on.

C. Botanical Extracts

It may be desirable to incorporate one more additional botanical extracts (other than those that contain an ingredient containing at least one linoleic acid moiety as a component) into the composition. If present suggested ranges are from about 0.0001 to 20%, preferably from about 0.0005 to 15%, more preferably from about 0.001 to 10%. Suitable botanical extracts include extracts from plants (herbs, roots, flowers, fruits, seeds) such as flowers, fruits, vegetables, and so on, including yeast ferment extract, *Padina pavonica* extract, *Thermus thermophilis* ferment extract, *Camelina sativa* seed oil, *Boswellia serrata* extract, olive extract, *Acacia dealbata* extract, *Acer saccharinum* (sugar maple), *Acidopholus, Acorus, Aesculus, Agaricus, Agave, Agrimonia*, algae, aloe, citrus, *Brassica*, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza glabra, Salix nigra, Macrocycstis pyrifera, Pyrus malus, Saxifraga sarmentosa, Vitis vinifera, Morus nigra, Scutellaria baicalensis, Anthemis nobilis, Salvia sclarea, Rosmarinus officianalis, Citrus limonum, Panax ginseng, Siegesbeckia orientalis, Fructus mume, Ascophyllum nodosum, Glycine soja* extract, *Beta vulgaris, Haberlea rhodopensis, Polygonum cuspidatum, Citrus aurantium dulcis, Vitis vinifera, Selaginella tamariscina, Humulus lupulus, Citrus reticulata* Peel, *Punica granatum, Asparagopsis, Curcuma longa, Menyanthes trifoliata, Helianthus annuus, Hordeum vulgare, Cucumis sativus, Evernia prunastri, Evernia furfuracea, Kola acuminata*, and mixtures thereof.

D. Biological Materials

Also suitable are various types of biological materials such as those derived from cells, fermented materials, and so on. If present such materials may range from about 0.001 to 30%, preferably from about 0.005 to 25%, more preferably from about 0.01 to 20%. Examples include fragments of cellular RNA or DNA, or probiotic microorganisms. Particularly preferred are RNA fragments.

E. Oils

In the event the compositions used in the method of the invention are in emulsion form, the composition will comprise an oil phase. Oily ingredients are desirable for the skin moisturizing and protective properties. Suitable oils include silicones, esters, vegetable oils, synthetic oils, including but not limited to those set forth herein. The oils may be volatile or nonvolatile, and are preferably in the form of a pourable liquid at room temperature. The term "volatile" means that the oil has a measurable vapor pressure, or a vapor pressure of at least about 2 mm of mercury at 20° C. The term "nonvolatile" means that the oil has a vapor pressure of less than about 2 mm. of mercury at 20° C.

1. Volatile Oils

Suitable volatile oils generally have a viscosity ranging from about 0.5 to 5 centistokes 25° C. and include linear silicones, cyclic silicones, paraffinic hydrocarbons, or mixtures thereof.

(a). Volatile Silicones

Cyclic silicones are one type of volatile silicone that may be used in the composition. Such silicones have the general formula:

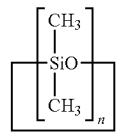

where n=3-6, preferably 4, 5, or 6.

Also suitable are linear volatile silicones, for example, those having the general formula:

where n=0, 1, 2, 3, 4, or 5, preferably 0, 1, 2, 3, or 4.

Cyclic and linear volatile silicones are available from various commercial sources including Dow Corning Corporation and General Electric. The Dow Corning linear volatile silicones are sold under the tradenames Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, a branched volatile silicone having the general formula:

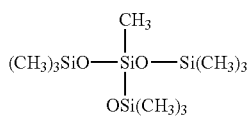

Methyl trimethicone may be purchased from Shin-Etsu Silicones under the tradename TMF-1.5, having a viscosity of 1.5 centistokes at 25° C.

(b). Volatile Paraffinic Hydrocarbons

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

2. Non-Volatile Oils

A variety of nonvolatile oils are also suitable for use in the compositions of the invention. The nonvolatile oils generally have a viscosity of greater than about 5 to 10 centistokes at 25° C., and may range in viscosity up to about 1,000,000 centipoise at 25° C. Examples of nonvolatile oils include, but are not limited to:

(a). Esters

Suitable esters are mono-, di-, and testers. The composition may comprise one or more esters selected from the group, or mixtures thereof.

(i) Monoesters

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

(ii). Diesters

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

(iii). Triesters

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety.

(b). Hydrocarbon Oils

It may be desirable to incorporate one or more nonvolatile hydrocarbon oils into the composition used in the method of the invention. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

(c). Glyceryl Esters of Fatty Acids

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

(d). Nonvolatile Silicones

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone.

For example, such nonvolatile silicones may have the following general formula:

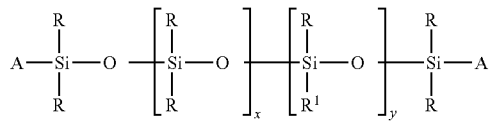

wherein R and R' are each independently $C_{1-30}$ straight or branched chain, saturated or unsaturated alkyl, phenyl or aryl, trialkylsiloxy, and x and y are each independently 1-1,000,000; with the proviso that there is at least one of either x or y, and A is alkyl siloxy endcap unit. Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the trade names Abil Wax 9801, or 9814.

F. Vitamins and Antioxidants

It may be desirable to incorporate one or more vitamins or antioxidants in the composition used in the method of the invention. If present, suggested ranges are from about 0.001 to 20%, preferably from about 0.005 to 15%, more preferably from about 0.010 to 10%. Preferably such vitamins, vitamin derivatives and/or antioxidants are operable to scavenge free radicals in the form of singlet oxygen. Such vitamins may include tocopherol or its derivatives such as tocopherol acetate, tocopherol ferulate; ascorbic acid or its derivatives such as ascorbyl palmitate, magnesium ascorbyl phosphate; Vitamin A or its derivatives such as retinyl palmitate; or vitamins D, K, B, or derivatives thereof.

G. DNA Repair Enzymes

The composition used in the method of the invention also contains at least one DNA repair enzyme. Suggested ranges are from about 0.00001 to about 35%, preferably from about 0.00005 to about 30%, more preferably from about 0.0001 to about 25% of one or more DNA repair enzymes.

DNA repair enzymes as disclosed in U.S. Pat. Nos. 5,077,211; 5,190,762; 5,272,079; and 5,296,231, all of which are hereby incorporated by reference in their entirety, are suitable for use in the compositions and method of the invention. One example of such a DNA repair enzyme may be purchased from AGI/Dermatics under the trade name Roxisomes®, and has the INCI name *Arabidopsis Thaliana* extract. It may be present alone or in admixture with lecithin and water. This DNA repair enzyme is known to be effective in repairing 8-oxo-Guanine base mutation damage.

Another type of DNA repair enzyme that may be used is one that is known to be effective in repairing 06-methyl guanine base mutation damage. It is sold by AGI/Dermatics under the tradename Adasomes®, and has the INCI name *Lactobacillus* ferment, which may be added to the composition of the invention by itself or in admixture with lecithin and water.

Another type of DNA repair enzyme that may be used is one that is known to be effective in repairing T-T dimers. The enzymes are present in mixtures of biological or botanical materials. Examples of such ingredients are sold by AGI/Dermatics under the tradenames Ultrasomes® or Photosomes®. Ultrasomes® comprises a mixture of Micrococcus lysate (an end product of the controlled lysis of various species of micrococcus), lecithin, and water. Photosomes® comprises a mixture of plankton extract (which is the extract of marine biomass which includes one or more of the following organisms: thalassoplankton, green micro-algae, diatoms, greenish-blue and nitrogen-fixing seaweed), water, and lecithin.

Another type of DNA repair enzyme may be a component of various inactivated bacterial lysates such as *Bifida* lysate or *Bifida* ferment lysate, the latter a lysate from *Bifido* bacteria which contains the metabolic products and cytoplasmic fractions when *Bifido* bacteria are cultured, inactivated and then disintegrated. This material has the INCI name *Bifida* Ferment Lysate.

Other suitable DNA repair enzymes include T4 Endonuclease V, which may be produced by the denV gene of the bacteriophage T4. Also suitable are base glycosylases such as uracil- and hypoxanthine-DNA glycosylases; apyrimidinic/apurinic endonucleases; DNA exonucleases, damaged-bases glycosylases (e.g., 3-methyladenine-DNA glycosylase); correndonucleases either alone or in complexes (e.g., *E. coli* uvrA/uvrB/uvrC endonuclease complex); APEX nuclease, which is a multi-functional DNA repair enzyme often referred to as "APE"; dihydrofolate reductase; terminal transferase; topoisomerase.

Other types of suitable DNA repair enzymes may be categorized by the type of repair facilitated and include BER (base excision repair) or BER factor enzymes such as uracil-DNA glycosylase (UNG); single strand selective monofunctional uracil DNA glycosylase (SMUG1); 3,N(4)-ethenocytosine glycosylase (MBD4); thymine DNA-glycosylase (TDG); A/G-specific adenine DNA glycosylase (MUTYH); 8-oxoguanine DNA glycosylase (OGG1); endonuclease III-like (NTHL1); 3-methyladenine DNA glycosidase (MPG); DNA glycosylase/AP lyase (NEIL1 or 2); AP endonuclease (APEX 1 and 2), DNA ligase (LIG3), ligase accessory factor (XRCC1); DNA 5'-kinase/3'-phosphatase (PNKP); ADP-ribosyltransferase (PARP1 or 2).

Another category of DNA repair enzymes includes those that are believed to directly reverse methylpurine damage such as 1-meA dioxygenase (ALKBH2 or ALKBH3).

Yet another category of enzymes operable to repair DNA/protein crosslinks includes Tyr-DNA phosphodiesterase (TDP1).

Also suitable are MMR (mismatch excision repair) DNA repair enzymes such as MutS protein homolog (MSH2); mismatch repair protein (MSH3); mutS homolog 4 (MSH4); MutS homolog 5 (MSH5); or G/T mismatch-binding protein (MSH6); DNA mismatch repair protein (PMS1, PMS2, MLH1, MLH3); Postmeiotic segregation increased 2-like protein (PMS2L3); or postmeiotic segregation increased 2-like 4 pseudogene (PMS2L4).

Also suitable are DNA repair enzymes known as nucleotide excision repair (NER) enzymes and include those such as Xeroderma pigmentosum group C-complementing protein (XPC); RAD23 (S. cerevisiae) homolog (RAD23B); caltractin isoform (CETN2); RFA Protein 1, 2, of 3 (RPA1, 2, or 3); 3' to 5' DNA helicase (ERCC3); 5' to 3' DNA helicase (ERCC2); basic transcription factor (GTF2H1, GTF2H2, GTF2H3, GTF2H4, GTF2H5); CDK activating kinase (CDK7, CCNH); cyclin G1-interacting protein (MNAT1); DNA excision repair protein ERCC-51; excision repair cross-complementing 1 (ERCC1); DNA ligase 1 (LIG1); ATP-dependent helicase (ERCC6); and the like.

Also suitable may be DNA repair enzymes in the category that facilitate homologous recombination and include, but are not limited to DNA repair protein RAD51 homolog (RAD51, RAD51L1, RAD51B etc.); DNA repair protein XRCC2; DNA repair protein XRCC3; DNA repair protein RAD52; ATPase (RAD50); 3' exonuclease (MRE11A); and so on.

DNA repair enzymes that are DNA polymerases are also suitable and include DNA polymerase beta subunit (POLB); DNA polymerase gamma (POLG); DNA polymerase subunit delta (POLD1); DNA polymerase II subunit A (POLE); DNA polymerase delta auxiliary protein (PCNA); DNA polymerase zeta (POLZ); MAD2 homolog ((REV7); DNA polymerase eta (POLH): DNA polymerase kappa (POLK): and the like.

Various types of DNA repair enzymes that are often referred to as "editing and processing nucleases" include 3'-nuclease; 3'-exonuclease; 5'-exonuclease; endonuclease; and the like.

Other examples of DNA repair enzymes include DNA helicases including such as ATP DNA helicase and so on.

The DNA repair enzymes may be present as components of botanical extracts, bacterial or yeast lysates, biological materials, and the like. For example, botanical extracts may contain DNA repair enzymes.

The compositions of the invention may contain one or more DNA repair enzymes. Preferably, the composition contains other ingredients that will provide a cosmetically or pharmaceutically acceptable product.

H. Preferred Compositions

Preferred compositions used in the method of the invention are in the aqueous solution or emulsion form and containing at least one polyunsaturated omega-6 fatty acid, optionally in combination with at least one DNA repair enzyme. In another preferred embodiment the composition contains a per1 gene activator consisting of a polyunsaturated omega-6 fatty acid.

More preferred is where the composition used in the method of the invention comprises at least one nonionic organic surfactant which is an alkoxylated alcohol and the at least one oil is an organic ester or hydrocarbon.

The invention will be further described in connection with the following examples which are set forth for the purposes of illustration only.

Example 1

A composition for use in the method of the invention was prepared as follows:

| Ingredient | % by weight |
| --- | --- |
| Caprylic/capric triglyceride | QS100 |
| Squalane | 9.50 |
| Aleurites Moluccana (Kukui) seed oil | 3.20 |
| Salvia hispanica seed extract/tocopherol | 1.00 |
| Bisabolol | 1.00 |
| Prunus armeniaca (Apricot) Kernel Oil | 1.00 |
| Caprylic/capric triglyceride/Salicornia herbacea extract | 0.50 |
| Tocopherol acetate | 0.20 |
| Linoleic acid | 0.20 |
| Cholesterol | 0.20 |
| Tetrahexyldecyl ascorbate | 0.10 |
| BHT | 0.09 |
| Anthemis nobilis (Chamomile) extract | 0.08 |
| Coffea arabica (coffee) seed extract | 0.05 |
| Magnolia officinalis bark extract | 0.05 |
| Vaccinium myrtillus seed oil | 0.02 |
| Garcinia Mangostana peel extract | 0.01 |

The composition is prepared by combining the ingredients and mixing well to form a liquid. The composition is stored in glass bottles.

Example 2

Various ingredients including those that contained polyunsaturated omega-6 fatty acids and those that did not were tested for per1 gene expression activity: Salvia hispanica (Chia) seed oil (12-23% linoleic acid), Prunus armenica (Apricot) oil (20-35% linoleic acid), Coffea arabica (coffee) seed extract (0% linoleic acid), alpha bisabolol (0% linoleic acid), Chamomile romaine oil (0% linoleic acid), and Magnolia extract (0% linoleic acid).

Normal human epidermal keratinocytes (NHEK) were diluted in EpiLife Media MEP1500CA with supplement S001-5 added (Gibco, Cascade Biologics, Invitrogen) to form a concentration of $3 \times 10^4$ and plated onto a black walled 96 well microtiter plate by adding 100 µl in each well. The plate was incubated for 3 hours at 37° C. in 5% $CO_2$. The media was removed and remaining adhered cells rinsed with EpiLife Media MEP1500CA, supplement free. A plasmid solution was prepared by diluting Tris-EDTA pH 8.0 buffer with plasmid pGL4.11 (DNA 2.0, Carlsbad, Calif.) to form a 1 mg/ml solution. This plasmid contained a per1 gene sequence and a luciferase reporter gene sequence. A transfection mixture was prepared by diluting EpiLife Media MEP1500CA, supplement free, to form a solution with 0.31 µg/ml of plasmid (obtained by adding appropriate amount of plasmid solution prepared above), 1.28% Plus™ Reagent (Catalog No. 11514-015, Invitrogen, Carlsbad, Calif.), and 3.22% Lipofectamine™ Transfection Reagent (Catalog No. 18324-012, Invitrogen, Carlsbad, Calif.). Transfection mixture, 40 was added to each well and the plate incubated for 4 hours at 37° C. in 5% $CO_2$. Then 80 µl of EpiLife Media MEP1500CA with supplement S001-5 was added to the well containing the control (media alone), the transfection mixture control (transfection mixture without any active ingredient). Test wells and transfection control wells. To the test wells 80 μl of test material solution (test material diluted in EpiLife Media MEP1500CA with supplement S001-5) was added. The wells were incubated for 16 hours at 37° C. in 5% $CO_2$. Immediately prior to reading, Bright-Glo™ (Pro-Mega, Madison Wis.) was added to each well plate in the same volume as is currently in the well (e.g. a 1:1 dilution). Luminescence was measured in an LMax™ Microplate Luminometer (Molecular Devices, Sunnyvale, Calif.). The results were as follows:

Positive Control (melatonin 100 uM concentration): 39.2% increase in per1
Negative Control: 0% increase in per1
Apricot kernel oil: 0.01% concentration: 14.3% increase in per1
Apricot kernel oil 0.05% concentration: 43.4% increase in per1
Apricot kernel oil: 0.1% concentration: 23.7% increase in per1
Chia extract: 0.01% concentration: 9.1% increase in per1
Chia extract: 0.05% concentration: 51.0% increase in per1
Chia extract: 0.1% concentration: 64% increase in per1
*Coffea arabica* (coffee) seed extract: 0.01% concentration: 0% increase in per1
*Coffea arabica* (coffee) seed extract: 0.05% concentration: 0% increase in per1
*Coffea arabica* (coffee) seed extract: 0.10% concentration: 0% increase in per1
alpha bisabolol: 0.01% concentration: 0% increase in per1
alpha bisabolol: 0.05% concentration: 0% increase in per1
alpha bisabolol: 0.10% concentration: 0% increase in per1
Chamomile romaine oil: 0.01% concentration: 0% increase in per1
Chamomile romaine oil: 0.05% concentration: 0% increase in per1
Chamomile romaine oil: 0.10% concentration: 0% increase in per1
Magnolia extract: 0.01% concentration: 0% increase in per1
Magnolia extract: 0.05% concentration: 0% increase in per1
Magnolia extract: 0.10% concentration: 0% increase in per1

The results demonstrate that Apricot kernel oil (20-35% linoleic acid) and Chia extract (12-23% linoleic acid) demonstrated significant increases in stimulating per1 gene expression in skin cells at various concentrations while the ingredients that did not contain a linoleic acid component had no effect on per1 gene expression.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

What we claimed is:

1. A method for increasing or synchronizing per1 gene expression in skin cells having decreased, irregular, or asynchronous per1 gene expression comprising topically applying to skin cells a composition comprising an ingredient selected from the group consisting of *Salvia hispanica* (Chia) extract, *Prunus armeniaca* (Apricot) kernel oil and mixtures thereof wherein the ingredient is characterized by causing an increase in per1 expression ranging from 9.1 to 64% when exposed to skin cells in vitro at a concentration within the range of 0.01 to 0.1%.

2. The method of claim 1 wherein the skin cells have decreased, irregular, or asynchronous per1 gene expression due to the natural aging process, or due to exposure to one or more of UV radiation, environmental pollution, environmental toxins, or physiological stress.

3. The method of claim 1 wherein the *Salvia hispanica* (Chia) extract contains from 12-23% linoleic acid.

4. The method of claim 3 wherein the *Prunus armeniaca* (Apricot) kernel oil contains from 20-35% linoleic acid.

5. The method of claim 1 wherein when a concentration within the range of 0.01 to 0.1% of *Salvia hispanica* (Chia) extract is exposed to cells in vitro the increase in per1 expression ranges from 9.1 to 64% respectively when compared to untreated cells.

6. The method of claim 1 wherein when a concentration within the range of 0.01 to 0.1% of *Prunus armeniaca* (Apricot) kernel oil is exposed to cells in vitro the increase in per1 expression ranges from 14.3 to 43.4% respectively when compared to untreated cells.

7. The method of claim 1 wherein the skin cells are keratinocyes.

8. The method of claim 1 wherein the composition in the form of a skin cream, lotion, foundation makeup, lipstick, concealer, blush, serum, eye shadow, cleanser or toner.

9. The method of claim 8 where the composition is applied to the skin in the evening prior to retiring.

10. A method for treating skin in a regimen comprising:
    (a) during the day treating the skin cells with a composition containing chemical or physical UV sunscreens;
    (b) at night, treating the skin cells that may have decreased, irregular, or asynchronous per1 gene expression due to UV exposure during the day, with a composition containing an extract from *Salvia hispanica* that is characterized by causing an increase in per1 gene expression in an amount ranging from 9.1 to 64% when tested on cells in vitro at a concentrations within the range of 0.01 to 0.1%.

11. A method for preparing a topical composition for treating skin cells that may have decreased, irregular, or asynchronous per1 gene expression by incorporating into the composition an ingredient selected from the group consisting of *Salvia hispanica* (Chia) extract containing from about 12-23% linoleic acid, *Prunus armeniaca* (Apricot) kernel oil containing from about 20-35% linoleic acid and mixtures thereof wherein when the *Salvia hispanica* (Chia) extract is characterized by causing an increase in per1 expression ranging from 9.1 to 64% when exposed to skin cells in vitro at a concentration within the range of 0.01 to 1% when compared to untreated cells and wherein the *Prunus armeniaca* (Apricot) kernel oil is characterized by causing an increase in per1 expression ranging from 14.3 to 43.4% when exposed to skin cells in vitro at a concentration within the range of 0.01 to 1%.

* * * * *